United States Patent [19]

McCullough et al.

[11] Patent Number: 5,666,983
[45] Date of Patent: Sep. 16, 1997

[54] APPARATUS FOR USING BEADED DENTAL FLOSS

[76] Inventors: Edward E. McCullough; Kevin W. McGaha, both of P.O. Box 46, Brigham City, Utah 84302

[21] Appl. No.: 519,204

[22] Filed: Aug. 28, 1995

[51] Int. Cl.[6] ................................................ A61C 15/00
[52] U.S. Cl. .................................................... 132/323
[58] Field of Search ............................ 132/323, 324, 132/327, 308, 309, 310; 206/63.5, 368, 369, 375

[56] References Cited

U.S. PATENT DOCUMENTS

| | | | |
|---|---|---|---|
| 3,474,799 | 10/1969 | Cappello | 132/323 |
| 4,753,254 | 6/1988 | McCullough et al. | 132/323 |
| 4,807,752 | 2/1989 | Chodorow | 132/324 |
| 5,067,503 | 11/1991 | Stile | 132/323 |

*Primary Examiner*—Cary E. O'Connor
*Attorney, Agent, or Firm*—Edward E. McCullough Agent

[57] ABSTRACT

A coilable structure having segments of dental floss mounted thereon, in parallel, tandem arrangement, is stored in a housing. A spindle in aft chamber thereof is attached to one end of the structure (in this case, a tape). Rotating the spindle aftwardly advances the tape so that the next floss segment is placed on the top of a partition between the chambers, positioning the segment slightly above and between a fixed and a sliding top member of the housing, where it can be grasped by an applicator having a handle and a pair of resilient prongs with slitted shoulders on their ends for retaining beads on ends of the floss segments. Aftwardly-convergent guides on the sliding top member compress the prongs together, as they are moved aftwardly between them by a user, prior to grasping a floss segment. Aftwardly-divergent guides on the fixed top member allow the prongs to expand without losing the floss they have grasped, as aftward motion of the prongs is continued. The coilable structure can also be stored in a removable cartridge that can be installed in the housing. Alternative embodiments are cited for advancing the coilable structure and for allowing the applicator prongs to expand in a controlled manner after having grasped a segment of floss.

35 Claims, 2 Drawing Sheets

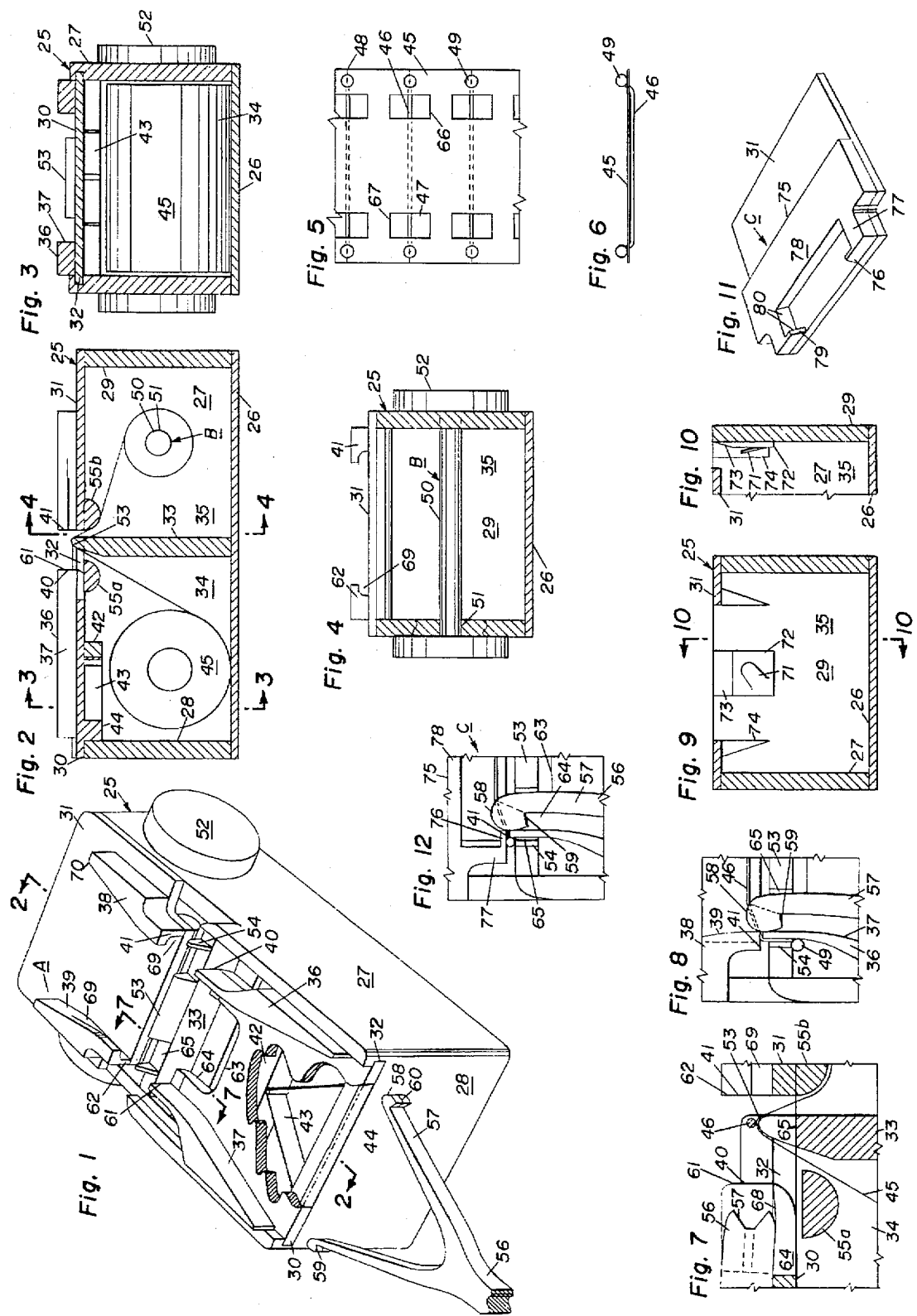

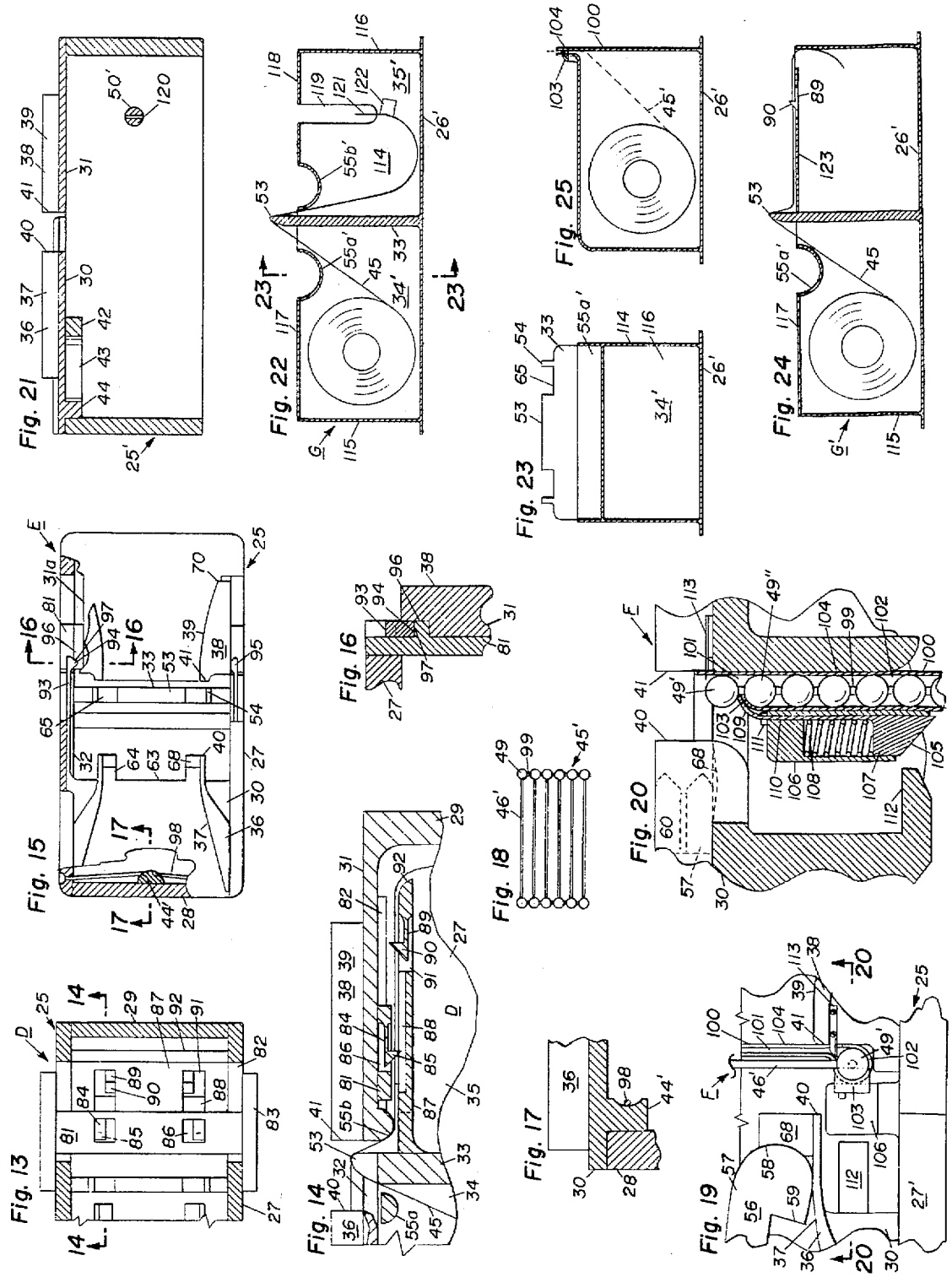

5,666,983

APPARATUS FOR USING BEADED DENTAL FLOSS

CROSS REFERENCES TO RELATED APPLICATIONS

This application is related to the following application, filed simultaneously herewith: "Coilable Structures Containing Beaded Dental Floss and Methods and Apparatus for Making Them," Ser. No. 08/519,714, filed 28 Aug. 1995, by Kevin W. McGaha and Edward E. McCullough.

BACKGROUND OF THE INVENTION

1. Field of the Invention

This invention relates to apparatus for storing dental floss and for loading it onto an applicator for use in dental hygiene. More specifically, it relates to apparatus capable of loading segments of floss, having beads fixed to their ends, onto an applicator having resilient prongs and means thereon for engaging the beads for retention of the floss. The invention relates, especially, to use with coilable structures that contain floss segments having beaded ends.

2. Description of the Prior Art

Dental floss having beads fixed to it, so that it can be grasped by resilient prongs of applicators, is known in the art, as are apparatus for loading such floss onto applicators.

An example of such apparatus is shown in U.S. Pat. No. 5,067,503, "Dental Apparatus for Flossing Teeth" by Thomas W. Stiles. This invention uses disposable, plastic cards, each of which holds a plurality of floss segments in a parallel arrangement. Each end of each floss segment is molded into a small, plastic bead that is a part of the card material and is fastened to the rest of the card by easily-breakable attachments. Cam surfaces on a housing guide the prongs of an applicator into holes in the card, so that the floss can be intercepted by slits in the prongs. A tug on the applicator then breaks the attachment of the beads to the card.

Another prior-art example is shown in U.S. Pat. No. 4,753,254 "Method and Apparatus for a Dental Floss System" by the present inventors, on which the present invention is regarded as an improvement. In this patent, a continuous strand of beaded floss is stored on a reel in a box-like container. The floss is drawn from the box through a small hole and is spaced above the surface of the box, by a pair of slotted supports, so that it can be intercepted by the slitted prongs of an applicator. A pair of convergent guides compresses the prongs of the applicator toward each other to grasp the floss between two adjacent beads thereon, as the applicator is moved between the guides. Small shoulders on these guides permit the prongs of the applicator to spring outwardly to grasp the floss between beads.

The Stiles invention is intended to operate with floss segments that are molded into a rigid, plastic card; and the second cited invention is intended to operate with a continuous strand of beaded floss. Hence, the present inventors are not aware of any apparatus that is capable of loading beaded dental floss onto an applicator, if the floss is neither molded to a plastic card nor has beads fixed to a continuous strand. Also, they are not aware of any prior existence of coilable structures containing beaded floss segments, nor of any apparatus capable of using such structures for loading dental-floss applicators with beaded dental-floss segments. Hence, there is a need for the present invention.

SUMMARY OF THE INVENTION

A primary object of the invention is to provide an apparatus that will load dental floss onto an applicator, wherein the floss is in short segments, each having a bead fixed to each of its ends.

Another object of the invention is to provide such an apparatus that will handle coilable structures that contain segments of beaded dental floss to load such floss segments onto an applicator.

Another object of the invention is to provide such an apparatus that will handle a coilable tape made of beaded floss segments wherein adjacent beads on the ends of parallel segments are joined together.

Primary features of the invention are that it is easy to use, reliable, and convenient.

Other features and advantages of the invention will be noted, as the following detailed description is read with reference to the drawings, wherein the same parts are designated by the same numbers throughout the disclosure.

BRIEF DESCRIPTION OF THE DRAWINGS

In the drawings:

FIG. 1 is an enlarged perspective view of a preferred form of the invention;

FIG. 2 is a sectional view taken on Line 2—2 of FIG. 1;

FIG. 3 is a full cross section taken on Line 3—3 of FIG. 2;

FIG. 4 is a full cross section taken on Line 4—4 of FIG. 2, but does not show paper tape on the take-up reel;

FIG. 5 is a fragmentary view of a paper tape loaded with beaded floss;

FIG. 6 is an end view of the coilable structure of FIG. 5;

FIG. 7 is a fragmentary, sectional view taken on the Line 7—7 of FIG. 1, and includes the end portion of the left-hand prong of an applicator plus a tape loaded with a floss segment;

FIG. 8 is a top view of the portion of the apparatus shown in FIG. 7, but shows the applicator prong advanced to the left-hand, divergent guide;

FIG. 9 is a sectional view showing the aft end of the housing, equipped with an optional apparatus for removing dental floss from an applicator;

FIG. 10 is a section taken on Line 10—10 of FIG. 9;

FIG. 11 is a perspective view of the fixed top member, showing an alternative embodiment of the device for controlling the expansion of applicator prongs, so that floss is properly loaded thereon;

FIG. 12 is a fragmentary, top view of the left-hand portion of FIG. 11, showing how it loads floss onto a prong of an applicator;

FIG. 13 is a sectional view of the aft-end portion of the invention (with the fixed top member removed), showing a second embodiment of the tape-advancing mechanism;

FIG. 14 is a sectional view taken on Line 14—14 of FIG. 13, but includes the fixed top member and divergent guides;

FIG. 15 is a top view of the invention, with some parts broken away, to show a third variation of the mechanism for advancing the tape;

FIG. 16 is a greatly-enlarged, sectional view taken on Line 16—16 of FIG. 15;

FIG. 17 is a similarly-enlarged view taken on Line 17—17 of FIG. 15;

FIG. 18 is a fragmentary top view of a coilable structure used in a fourth embodiment of the tape-advancing means;

FIG. 19 is a fragmentary top view of a modified, forward edge portion of the fixed top plate to show the fourth embodiment of the means for advancing the tape;

FIG. 20 is a sectional view taken on Line 20—20 of FIG. 19;

FIG. 21 is a view similar to FIG. 2, but shows an alternative embodiment of the housing that can be used with a disposable cartridge;

FIG. 22 is also similar to FIG. 2, but shows a disposable cartridge that can be used with the housing of FIG. 21;

FIG. 23 is a full cross section taken on Line 23—23 of FIG. 22;

FIG. 24 is similar to FIG. 22, but shows a cartridge that can be used with the second and third embodiments of the means for advancing the tape; and FIG. 25 is also similar to FIG. 22, but shows a cartridge that can be used with the fourth embodiment of the means for advancing the tape.

DESCRIPTION OF THE PREFERRED EMBODIMENTS

As shown in FIGS. 1–4, the invention has a housing 25 having a bottom member 26, two identical side members 27, two identical end members (a forward end 28 and an aft end 29), a movable or sliding top member or plate 30, and a fixed top member or plate 31. In a preferred form of the invention, the sliding top plate 30 is supported in two parallel grooves 32 in the upper, inner portions of the two side members 27. The grooves 32 extend from the forward ends of the side members 27 to approximately half their lengths. In its normal position, the sliding top plate 30 is spaced about ½ inch from the fixed top plate 31, and in the same plane. Under the space between these top plates, a transverse partition 33 divides the housing 25. Together with the bottom member 26, the sides 27, the forward end 28 and the sliding top 30, this partition defines a first storage chamber 34. And, together with the bottom 26, the sides 27 the aft end 29 and the fixed top member 31, the partition 33 defines a second storage chamber 35.

For the sake of clarity, all motions and positions of parts are described in relation to the forward end 28 or aft end 29 of the housing 25. Hence, "aftward" motion is toward the aft end of the housing and a "forward" edge is an edge nearest the forward end of the housing.

A convergent set of juxtaposed, mirror-image, guide members 36, having inner surfaces 37 convergent aftwardly, is integral with the top of the sliding top plate 30. A similar, divergent set of juxtaposed, mirror-image, guide members 38 is integral with the fixed top plate and has inner surfaces 39 divergent aftwardly. The inner surfaces 39 are continuous with those 37 of the convergent guide members 36 when the sliding top plate 30 is moved so that the aft ends 40 of the convergent guide members 36 contact the forward ends 41 of the divergent guides 38. The guide members 38 comprise a means A for controlling the expansion of the prongs 57 of an applicator after they have been loaded with a floss segment so that it does not escape from the prongs.

A first transverse bar 42, fixed at its ends to the sides 27 of the housing 25, holds a forwardly-extending, double-leaf spring 43 that bears against a second transverse bar 44 fixed to the underside of the movable top plate 30. The spring 43 forces the second bar 44 against the forward end 28 of the housing 25 to maintain the movable top plate 30 in a normally-forward position, spaced away from the fixed top plate 31. The second bar 44 could be replaced any of various protrusions on the movable top plate 30 that could function as a stop means against an obstruction on the housing 25 and provide a bearing means for the spring 43.

A roll of paper tape 45 (FIGS. 2, 5, 6, 14, 22 and 24), loaded with segments of beaded dental floss 46, is stored in the first chamber 34. The tape 45 (FIG. 5) has pairs of juxtaposed, rectangular holes 47, and a pair of tiny slits 48 in the edges of the tape 45 coincident with a centerline passing through each pair of holes 47. Each segment of floss 46 has a bead 49 fixed to each of its ends, and it is mounted to the tape by having its beads 49 extend through the slits 48 so that they are on the side of the tape opposite from the rest of the floss segment (FIG. 6). As shown in FIG. 5, the mounted floss segment extends across the centers of the holes 47.

FIG. 2, shows the paper tape 45 passing over the upper portion of the partition 33 (with the floss on the upper side of the tape) and then into the second storage chamber 35, where its end portion is inserted into a slit 120 in the reel shaft 50 and the tape 45 is manually wound thereon. The ends of this shaft are journaled in holes 51 in the sides 27 of the housing 25 (FIG. 4), and are fixed to thumbwheels 52 on the outside of the housing. This reel comprises a means B for advancing the tape.

As shown in FIGS. 1, 2 and 3, the upper, central portion of the partition 33 is raised, relative to the remainder thereof, to provide a transverse tape support 53 for the central portion of the paper tape 45 without obstructing the holes. Two optional, auxiliary tape supports 54, having the same height as the tape support 53, support the portions of the tape 45 between the holes 47 and the beads 49. These auxiliary supports 54 are desirable if, in their absence, the tape 45 is too flexible to hold the beads 49 in positions such that the floss is easily grasped by prongs of an applicator. The functions of the tape supports 53 and 54 are independent of that of the partition 33. Hence, it is merely a matter of convenience and manufacturing expediency that they comprise the upper portion of the partition. In fact, the partition 33 could be thought of as being merely a downward extension of the transverse tape support 53.

A first, transverse, curved guide 55a, fixed to the inside of the housing 25, guides the tape 45 so that it passes near the partition 33 and away from the motion of the sliding top plate 30. A second, transverse, curved guide 55b, fixed to the under side of the forward edge of the fixed top plate 31 guides the tape 45 smoothly into the second storage chamber 35.

To practice the invention, an applicator 56 of the type described in U.S. Pat. No. 4,776,357 is used (FIGS. 1, 7, 8, 12, 19 and 20). This applicator 56 has two resilient prongs 57, the rounded ends 58 of which partially define outwardly-extending shoulders 59. Slits 60 in the ends of the prongs 57 lie in the plane of the prongs and extend through the shoulders 59, so that they can intercept a segment of floss 46 and trap a bead 49 of the floss behind each of the shoulders 59. The resilient prongs 57 bear outwardly against the beads 49, so that the floss cannot escape from the applicator 56 by being pulled in any direction; and it is maintained under tension by the prongs.

The user begins the process of loading floss 46 onto the applicator 56 by rotating either of the thumbwheels 52 aftwardly to advance the paper tape 45 until a segment of floss 46 lies directly on top of the tape supports 53 and 54. This places the floss 46 in position to be intercepted by the slits 60 in the prongs 57.

The prongs 57 of the applicator 56 are then inserted between the convergent, inner surfaces 37 of the convergent guide members 36. Aftward movement of the applicator then simultaneously compresses the prongs 57 toward each other and moves the sliding top plate 30 until the aft ends 40 of the guide members 36 contact the forward ends 41 of the divergent guide members 38. The forward-end surfaces 62 of the divergent guide members 38 are spaced slightly aft of the floss segment being held on the tape support 53, so that the floss 46 is clamped under tension between the vertical surfaces 61 and 62 of the two sets of guide members 36 and 38. This makes the floss more easily grasped by the slits 60 in the applicator prongs 57 (FIG. 7). It also causes the floss 46 to be pulled by the applicator prongs at an angle to the tape 45 such that the beads 49 may be removed therefrom without tearing the paper.

Clamping of the floss 46 between the vertical end surfaces of the two sets of guide members 36 and 38 is made possible by the fact that the aft end portions 40 of the convergent guides 36 are narrowed (as viewed from the top), parallel, and extend beyond the aft edge 63 of the sliding top member 30. They are supported by short, narrow extensions 64 of the sliding top plate 30. These extensions 64 also support the prongs 57 of the applicator 56 when they reach the aft-end portions 40 of the convergent guides 36. The shoulders 65 on either side of the tape support 53 provide the dual functions of supporting the extensions 64 and guiding them into vertical alignment with the fixed top plate 31, as the sliding top plate 30 is moved aftwardly. Also, when the tape 45 is advanced so that a segment of floss 46 thereon is placed squarely on top of the tape support 53, the tape is folded vertically over this support, so that the forward and aft edges 66 and 67 (FIG. 5), respectively, of the corresponding pair of holes 47 in the tape are approximately coincident with the forward and aft edges of the shoulders 65 (FIGS. 7 and 8). Hence, when the extensions 64 of the sliding top plate 30 are moved over these shoulders, they pass through the folded holes 47 and cooperate with the shoulders 65 to prevent the tape 45 from moving while the applicator 56 pulls a floss segment 46 therefrom. The width dimensions of an aft-end portion 40 of a guide 36, its supporting extension 64 of the top plate 30, and the end portion of an applicator prong 57 are such that they are all able to pass through a folded hole 47 of the paper tape 45 simultaneously.

As the prongs 57 of the applicator 56 advance between the convergent surfaces 37, they encounter a small, raised portion or incline plane 68 on the end portion of each extension 64 of the top plate 30. These raised portions provide resistance against which the applicator prongs 57 bear, after the aft-end portions 40 of the convergent guides 36 become parallel. This insures that their end portions 40 can clamp the floss 46 against the divergent guides 38 without the top plate 30 being returned prematurely to its original position by the spring 43, or before the applicator prongs can engage the divergent surfaces 39 of the divergent guides 38 to maintain their state of compression after having grasped a segment of floss.

A small amount of lateral looseness in the fit between the sliding top plate 30 and its grooves 32 in the housing sides 27 is desirable for easy operation thereof. It also permits the outer curves on the shoulders 59 of the applicator prongs to automatically align the convergent surfaces 37 with the divergent surfaces 39 when the prongs are being moved aftwardly at the juncture of these surfaces.

In a preferred design of the applicator 56, each of its prongs 57 is laterally flexible along its entire length. Hence, when the end portions thereof are compressed together, the remainder of each prong typically bows outwardly, relative to the ends, leaving no room between the prongs and the divergent surfaces 39 for the beads 49 (which, after having been grasped by the slits 60 of the prongs 57, trail behind the prong shoulders 59 as they move aftwardly). Hence, a channel 69 (FIGS. 1 and 4) is provided in each of the divergent surfaces 39 to accommodate passage of a bead 49. These channels 69 become increasingly shallow as the divergent surfaces 39 progress aftwardly and they end at about two thirds of the lengths of these surfaces. This is because, as the prongs 57 expand between the divergent surfaces 39, the floss 46 is taken up and the prongs become less bowed, so that the beads 49 then fit snugly behind the shoulders 59 of the prongs before they pass beyond the aft ends of the divergent surfaces 39. These surfaces 39 end with sharp corners 70 before the prongs 57 of the applicator 56 expand completely; so that, when shoulders of the prongs reach these corners, they snap outwardly, using the corners to force the beads 49 inwardly to insure that they are behind the prong shoulders 59.

FIGS. 9 and 10 show a simple (optional) means of removing used floss from an applicator 56. A small cutting tab 71 is fixed to a small, raised portion 72 on the inside of the upper-central portion of the aft end 29 of the housing 25. The height of this raised portion is equal to about half the thickness of the applicator prongs 57 and it is integral with a short ramp 73 that guides the floss 46 of the loaded applicator 56 under the cutting tab 71. The used floss may be severed simply by inserting the prongs of the applicator into the aft end portion of the housing 25 and pressing the floss beneath the cutting tab 71. Two wedge-shaped protrusions 74, fixed to the aft end 29 on either side of the cutting tab 71 may then be used for scraping the beads 49 from the shoulders 59 of the prongs 57, so that the used floss falls into the second storage chamber 35. Although this means of removing used floss from an applicator is shown mounted on the inside of the housing 25, it could just as well be mounted on the outside thereof (i.e., on the other side of the aft end 29); so that used floss can be discarded directly into a waste basket, rather than stored inside the housing 25.

FIGS. 11 and 12 show an alternative means C of loading the floss onto the applicator by controlling the expansion of the prongs thereof. The divergent guide members 38 are eliminated and replaced with a floss-loading member 75 having the general shape of an inverted "U" with short, inwardly-extending serifs or flanges 76. Each of the two parallel bars 77 of the "U" shape is integral at its forward end with a flange 76 and at its aft end with a cross bar 78, that joins the parallel bars 77. As shown in FIG. 12, the aft-end portions 40 of the guides 36 are spaced apart so that the convergent surfaces 37 thereof match the inner surfaces 79 of the flanges 76. When the applicator 56 is moved between the convergent surfaces 37, so that the slits 60 in the prongs 57 intercept a segment of floss 46, they push the floss aftwardly until the shoulders 59 of the prongs 57 snap past the flanges 76. This sudden expansion of the prongs uses these flanges to force the floss deeply into the side slits 60 in the shoulders of the prongs. Then, when the prongs are lifted from the loading device 75, the beads 49 (which have been separated from the shoulders of the prongs by the flanges 76) are pulled upwardly until they are finally trapped beneath the shoulders 59 of the prongs as they are freed from the loading device and snap outwardly to complete their expansion. Removal of the prongs 57 from the loading device 75 is facilitated by upwardly-divergent surfaces 80 on the inner sides of the bars 77 and inner ends of the flanges 76. Each of these surfaces 80 diverges about 10 degrees from the vertical. Hence, the resilient prongs 57, pressing outwardly against these surfaces 80, assist in their own upward removal from the loading device 75.

FIGS. 13 and 14 show a second embodiment D of the means for advancing the tape 45. In this version, the thumbwheels 52 and the reel shaft 50 are eliminated and replaced by a sliding advance bar 81. The ends of this bar extend through slots 82 in the sides 27 of the housing 25, and the bar 81 is manually moved forwardly and aftwardly by buttons 83 fixed to its ends. A pair of leaf springs 84, having downwardly-extending hooks 85 on their end portions, are fixed, at their other ends, in the aft ends of slots 86 in the bar 81, which is essentially a movable support for the hooks 85.

A flat, tape-support plate 87 is fixed at its forward end to the partition 33 and extends horizontally beneath the bar 81. It is sufficiently spaced therefrom to allow free passage of the tape 45 between the bar and the plate. Hence, the plate 87 is essentially a tape-support or tape-backing member. The first set of hooks 85 extends through the holes 47 in the tape 45 and into slots 88 in the plate 87. By this means, they are able to engage the aft edges of the holes in the tape to advance the tape when either of the buttons 83 is moved aftwardly by the user. The length of each slot 82 is such that it permits the tape 45 to advance through the exact distance between adjacent floss segments 46 thereon, when a button 83 is moved aftwardly by a user. A second set of leaf springs 89, each having an upwardly-extending hook 90 on one end and fixed at its other end to the aft end of a slot 91 in the plate 87, also engages the aft edges of the holes 47 in the tape 45. However, these hooks 90 do not move the tape, but simply prevent it from moving forwardly as the bar 81 is returned to engage the next set of holes 47 in the tape 45 with the first set of hooks 85. As the tape is advanced by this means, it falls off the aft edge 92 of the plate 87 and into the second storage chamber 35. The natural curl of the tape from having been stored as a coil in the first chamber 34 causes it to form a similar coil in the second storage chamber. Each set of hooks 85 or 90 has about a 45 degree cam on the side opposite the hook surface to enable the hook to slide over the tape 45 when being moved to engage the next hole 47 therein.

FIGS. 15, 16, and 17 show a third embodiment E of the means for advancing the tape 45. Instead of manually moving the tape-advance bar 81 by the buttons 83, these buttons are eliminated and replaced by two long, parallel push bars 93, spring-biased toward each other. Each is fixed at one end to the underside of the sliding top plate 30, and extends into the second storage chamber 35. Each has a small prominence 94 on the inner side of its free-end portion 95. Two vertical flanges 96 are fixed to the upper surface of the advance bar 81, and each has a small cavity 97 in its outer surface that can engage the prominence 94 on its corresponding push bar 93 to form a slip joint (the prominences can slip in and out of engagement with the cavities). These push bars are sufficiently long that their prominences 94 engage the cavities 97 in the flanges 96 when the sliding top plate 30 is in its normal position (spaced away from the fixed top plate 31). Then, when the prongs 57 of the applicator 56 engage the convergent surfaces 37 of the convergent guide members 36, the advance bar 81 moves aftwardly as far as the slots 82 in the sides 27 of the housing 25 permit. Further force exerted by the applicator overcomes the spring pressure of the push bars 93, causing their prominences 94 to move out of engagement with the cavities 97 in the flanges 96. This permits the sliding top plate 30 to continue its aftward motion to confine the floss 46 between the two sets of guides 36 and 38, after the tape 45 has been advanced by the advance bar 81.

In this embodiment of the tape-advancing means, the leaf spring 43, which returns the sliding plate 30 to its normal position, is eliminated and replace by an elastic filament 98, since the sliding top plate 30 must move through a greater distance than in the previously-described, tape-advancing means. The central portion of the filament 98 bears against a semi-cylindrical post 44' fixed to the underside of the sliding top plate 30. When the sliding top plate 30 is in its normal position, the prominences 94 and cavities 97 are again engaged. It is apparent that the push bars 93 would operate equally well, relative to the flanges 96, if the prominences were on the flanges and the cavities were in the end portions of the push bars.

In the tape-advancing means D, the buttons 83 serve, not only for moving the advance bar 81, but also bear against the sides of the housing to prevent the advance bar from rotating about a vertical axis. This latter function is accomplished in the present embodiment by the longitudinal edges 31a of the top plate 31, against which the flanges 96 bear (FIG. 15).

FIGS. 19, 20 and 25 show a fourth embodiment E of the means for advancing a tape containing beaded segments of dental floss. The paper tape 45 is not used; because the tape 45' of this embodiment is made by attaching the beads 49 on the ends of the floss segments directly to one another by tiny isthmuses or necks 99 to form a coilable structure comprising contiguous, parallel segments of floss 46' (FIG. 18). The floss 46' is sufficiently stiff that the tape 45' maintains a given width, so that it can be handled by the apparatus shown. Also, in this embodiment, a coil of the tape 45' is preferably contained in a thin-walled cartridge or container 100 for easy handling (FIGS. 19, 20 and 25). The cartridge 100 is closed, except at its upper, aft edge, where a long, transverse slot 101 is formed for dispensing the floss segments. The end portions 102 of the slot 101 are circular in cross section to accommodate the beads 49, and they are wider than the slot to provide lateral support for the beaded edges of the tape 45' (FIG. 19). At the forward side of each end portion 102 of the slot 101 is a leaf spring 103 that bears aftwardly against the neck 99 between a bead 49' of the end segment of floss and one 49" of the penultimate segment; so that the end segment is positioned for use by other apparatus, and the rest of the tape 45' is kept enclosed in the cartridge 100. The leaf springs 103 are preferably integral with the cartridge 100 and are biased toward the aft walls 104 of the end portions 102 of the slot 101, which are extended upwardly sufficient to provide backing support for the beads 49' (FIGS. 20 and 25). Optionally, if the tape 45' is not enclosed in a cartridge, the leaf springs 103 may be operatively fixed to the housing 25.

A pair of spring-loaded cams 105 is operatively attached to the sides 27 of the housing 25. Each of the pair is spaced forwardly of a row of beads 49 in the cartridge 100, and is enclosed in a barrel 106 that is square in cross section to fit the form of a piston 107, with which the cam 105 is integral. A compression spring 108 is confined inside the barrel 106 between the top of the piston 107 and the top of the barrel to urge the piston (and cam 105) downwardly. An upwardly and aftwardly extending leaf spring 109 is fixed to the top of each piston 107 so that it extends through a slit 110 in the top of its respective barrel 106. This spring 109 also normally bears against the neck 99 that joins the end bead 49', and the penultimate bead 49" of its respective row of beads, when a cartridge of floss segments is in place. A small pin 111 is fixed to the spring 109 to provide a stop means to prevent the piston 107 from falling out of the barrel 106.

When a floss applicator 56 in the hands of a user moves the top plate 30 aftwardly, cam-operating projections 112, fixed to the underside of the movable top plate, move the cams 105 and their leaf springs 109 upwardly. This advances the end pair of beads 49' so that their floss segment 46' can be easily grasped by the prongs 57 of the applicator 56 before the convergent guides 36 on the movable top plate 30 contact the divergent guides 38 on the fixed top plate 31. The applicator prongs 57 then interact with the means A or C for controlling their expansion, as described in the embodiments cited above.

Optionally, a pair of tiny knives 113 or cutting tabs may be fastened to the fixed top plate 31 near the forward edge thereof and adjacent the insides of the necks 99 between the end beads 49' and the penultimate beads 49" to insure separation thereof. The cartridge 100 is equipped with a bottom member 26' that replaces the bottom member 26 of the housing 25, and the upper, aft portions of its sides 27' are cut away to accommodate the barrels 106.

FIGS. 21–24 show an alternative embodiment of the previously-described forms of the invention, wherein the tape 45 is stored in disposable cartridges G, and G'. In this embodiment, the housing 25' has no bottom member. Hence, it can be slipped over the top of the cartridge. The bottom of the cartridge G then becomes the bottom member 26' of the housing 25'. Comparing this embodiment of the invention to that shown in FIG. 2, it can be seen that certain parts are now omitted from the main housing 25', but are included in the cartridge. These parts (FIG. 2) are: (1) the bottom member 26; (2) the partition 33; (3) the tape supports 53 and 54; (4) the curved guides 55a and 55b; and (5) the tape 45.

The cartridge G is essentially a rectangular box. In addition to its bottom member 26', it has two identical side members 114, a forward-end member 115; an aft-end member 116; a forward top member 117, the aft edge of which curves downwardly then upwardly to form a first tape guide 55a'; and an aft top member 118, the forward edge of which curves downwardly then upwardly to form a second tape guide 55b'. A vertical slot 119, open at the top, in each side member 114 accommodates the reel shaft 50', which, has a longitudinal slit 120 in it to receive the narrowed, free end 121 of the paper tape 45. The end 121 of the tape 45 is held in a vertical position in alignment with the center of the slit 120 by a small piece of adhesive tape 122. This adhesive tape is easily broken when the end 121 of the tape 45 is fitted into the shaft slit 120 and the shaft 50' is rotated. The cartridge is divided into a first storage chamber 34' and a second storage chamber 35' by a partition 33. The upper portion of the partition 33 is formed into a tape support 53 and ancillary tape supports 54, similar to the supports 53 and 54 shown in FIGS. 1, 2 and 3.

When the cartridge G is installed in the housing 25', the resulting apparatus operates in a manner identical to that shown in FIGS. 1 and 2.

As shown in FIG. 24, the embodiments D and E of the tape-advancing means require a slightly modified configuration for the upper portion of the cartridge. FIG. 24 shows the cartridge G' that is used with these embodiments. This is essentially the same as the cartridge G, except that it has no slot 119 to accommodate a reel shaft 50' and the aft portion 123 of the top of the cartridge is entirely flat, joins the partition 33, and functions as the horizontal tape-supporting plate 87 In this embodiment, the cam hooks 90 and the second set of leaf springs 89 are an integral part of the aft-top portion 123 of the cartridge G'.

Although the invention has been described herein with considerable specificity and detail, it should be noted that many alternative designs would fall within the spirit and scope of the invention. Hence, these should not be limited, except as defined in the following claims. For example, certain elements included in the cartridges and eliminated from the housings could just as well be included in the housings.

The invention claimed is:

1. Apparatus for loading dental-floss segments onto an applicator, wherein each segment has a bead fixed to each of its ends, the segments are mounted in a coilable structure perpendicular to the longitudinal axis thereof, and wherein the applicator is of the type having a handle fixed to a pair of resilient prongs and means at their ends for grasping a segment of floss and retaining the beads there of, comprising:

housing means for storing said coilable structure;

means for advancing the coilable structure, so that a floss segment thereon is positioned to be grasped by an applicator;

means for guiding and compressing the prongs of an applicator for grasping a floss segment therewith; and means for controlling expansion of the prongs after a floss segment has been grasped, so that the beads thereon are retained by the prongs.

2. The apparatus of claim 1 wherein the housing means has a fixed top member; a movable top member, normally spaced away from the fixed top member; and means for retaining the movable top member on the housing so that it can be moved toward and away from the fixed top member.

3. The apparatus of claim 2 further including means for returning the movable top member to its normal position, spaced away from the fixed top member, after being moved from that position.

4. The apparatus of claim 3 wherein the means for returning the movable top member to its normal position comprises spring means bearing against the movable top member and the housing so that the movable top member is biased away from the fixed top member.

5. The apparatus of claim 2 wherein the housing has two side members, a forward-end member and an aft-end member, and wherein the movable top member engages at least one of the side members for sliding motion.

6. The apparatus of claim 5 wherein the movable top member engages grooves defined in the inside surfaces of the upper portions of the side members.

7. The apparatus of claim 2 wherein the coilable structure comprises a tape, and wherein part of the means for manipulating the coilable structure comprises a transverse support member, fastened to the housing, having a raised central portion for supporting the tape so that a floss segment thereon is positioned relative to the top members so that it can be easily grasped by applicator prongs sliding aftwardly thereon.

8. The apparatus of claim 7, wherein the tape has pairs of opposing slits in its edges as a means of mounting the floss segments thereon (the end portions of the tape extending through the slits so that the beads are on the side of the tape opposite that of the floss), further including narrow, auxiliary supports on the tape-support member, having substantially the same height as said central portion thereof, for supporting the tape adjacent the beads.

9. The apparatus of claim 7 wherein the means for guiding and compressing the prongs of an applicator comprises a pair of mirror-image, convergent guides on the movable top member, having inner surfaces convergent aftwardly, whereby the prongs of an applicator are compressed when moved aftwardly between them.

10. The apparatus of claim 9 wherein the tape defines tandem pairs of holes therein and each floss segment extends across each hole of a pair, and wherein the aft-end portions of the convergent guides become parallel and extend beyond the aft edge of the movable top member; including small extensions of the top member that extend beneath the aft-end portions of the convergent guides for support thereof, so that these extensions and guides can slide over the transverse tape support on either side of its raised portion, and through the holes in the tape, which are folded over the tape support, to contact the means for controlling expansion of applicator prongs and to confine a segment of floss therebetween, whereby the extensions of the top member not only hold the tape in place while a segment of floss is removed therefrom by the prongs of an applicator, but also provide support for the prongs of an applicator as it is moved aftwardly by a user.

11. The apparatus of claim 10 further including a small raised portion on the surface of each extension of the movable top member, against which the prongs of an applicator may bear, to prevent the movable top member from returning to its normal position before the compressed prongs of the applicator pass from the convergent guides to the means for controlling expansion of said prongs.

12. The apparatus of claim 2 wherein the means for controlling expansion of applicator prongs comprises a pair of divergent, mirror-image guides, fastened to the fixed top member, having inner surfaces that are aftwardly-divergent, whereby the compressed prongs of an applicator, loaded with a floss segment, can pass from the means for compressing and guiding the prongs of an applicator to said divergent guides and expand therebetween without losing the floss, as the prongs are moved aftwardly by a user.

13. The apparatus of claim 12 wherein each of the divergent, inner surfaces defines a longitudinal groove therein to facilitate passage of a bead on a floss segment, as an applicator, loaded with floss, is moved aftwardly between them.

14. The apparatus of claim 12 wherein the distance between the aft ends of the divergent guides is less than the outer span of the shoulders of the applicator prongs, so that the prongs snap outwardly when moved past said ends of the guides, whereby said ends press the beads of the floss beneath the shoulders of the prongs for secure retention of the beads.

15. The apparatus of claim 2 wherein the means for controlling expansion of applicator prongs after a floss segment has been grasped thereby comprises two juxtaposed, parallel bars extending aftwardly on the fixed top member and a short, inwardly-extending, flange on the forward end of each bar, positioned so that the compressed prongs of an applicator, loaded with a floss segment, are received between said flanges from the means for compressing and guiding the prongs, and are allowed to expand aft of the flanges, which press the end portions of the floss into slits in the shoulders of the prongs as they expand.

16. The apparatus of claim 15 wherein the inner surfaces of the parallel bars and of their flanges are upwardly divergent, to facilitate removal of applicator prongs therefrom; and further including a cross bar joining the aft ends of the parallel bars, to provide a positive stop for the prongs of an applicator.

17. The apparatus of claim 1 wherein the coilable structure comprises a tape and wherein part of the means for manipulating it comprises a means for advancing the tape to position each floss segment thereon, successively, so that it can be easily grasped by compressed prongs of an applicator.

18. The apparatus of claim 17 wherein the means for advancing the tape comprises a transverse shaft, journaled in the housing, the housing defining a hole through which an end portion of the shaft extends, so that the shaft can be manually rotated thereby; and means for attaching the tape to the shaft.

19. The apparatus of claim 18 wherein the shaft defines a longitudinal slit therein, as the means for attaching a tape thereto.

20. The apparatus of claim 17 wherein the tape defines holes therein and the means for advancing-the tape comprises: hook-and-cam means, resiliently biased toward the tape, capable of penetrating a hole in the tape and the hook means engaging an aft edge thereof; a support for the hook-and-cam means to which it is attached, slidably engaged to the housing, so that aftward movement of the hook means, engaging a hole, advances the tape, and forward movement thereof causes the cam means to slide over the tape so that the hook means engages the next adjacent hole; and means for moving the hook-and-cam means to advance the tape by increments.

21. The apparatus of claim 20 wherein the support for the hook-and-cam means comprises a transverse bar, to which the hook-and-cam means is resiliently attached, slidably engaged to the housing; wherein the means for moving the hook and cam means comprises an end portion of the bar that extends through a slot defined in the housing, so that it can be manually moved forwardly and aftwardly thereby; and means for limiting the travel of the bar, relative to the tape, so that the hook means engages a hole in the tape with accuracy and advances it the distance between floss segments mounted thereon.

22. The apparatus of claim 20 further including means for preventing the aftwardly-advanced tape from moving forwardly.

23. The apparatus of claim 22 further including a tape-backing member attached to the housing so that it supports the tape to facilitate penetration of the holes therein by the hook-and-cam means; and wherein the means for preventing the tape from moving forwardly comprises: a second hook-and-cam means, fastened to the tape-backing member, resiliently biased toward the tape, and positioned to penetrate a hole in the tape and the hook means to engage an aft edge thereof.

24. The apparatus of claim 20 wherein the support for the hook-and-cam means comprises a transverse bar, and the means for moving the hook-and-cam means comprises at least one resilient push bar, attached at one end to the movable top member; a slip joint whereby the free end of the push bar engages the transverse bar, so that the travel of the movable top member can be greater than that of the transverse bar; and means for limiting the travel of the transverse bar, relative to the tape, so that the hook means engages a hole in the tape with accuracy and advances it the distance between floss segments mounted thereon, whereby the tape is advanced automatically when the movable top plate is moved aftwardly.

25. The apparatus of claim 24 wherein the slip joint comprises a prominence on one of the members engaged thereby, and a cavity defined in the other member, so that the prominence and cavity can be moved into and out of mutual engagement, the resilience of said push bar biasing it toward engagement with the transverse bar.

26. The apparatus of claim 1 wherein the coilable structure comprises a tandem series of parallel floss segments, each having a bead fixed to each end, wherein beads of adjacent segments are fastened together to produce a row of beads on each edge of the coilable structure, and wherein the means for manipulating the coilable structure comprises apparatus for advancing the end floss segment, comprising: means for guiding the coilable structure so that its end segment of floss is easily grasped by the prongs of an applicator; means for holding the portion of the coilable structure, adjacent the end segment, securely while the end segment of floss is removed therefrom; and means for advancing the new end segment of the coilable structure to replace one that has been removed.

27. The apparatus of claim 26 wherein the means for guiding the tape comprises a pair of juxtaposed, vertical channels in which the rows of beads at the edges of the tape can ride, the channels being operatively fastened to the housing and spaced apart to fit the rows of beads.

28. The apparatus of claim 26 wherein the means for holding the end portion of the coilable structure comprises spring means, operatively attached to the housing, for holding a pair of beads near the end segment of said coilable structure in place, relative to the housing.

29. The apparatus of claim 26 wherein part of said housing means comprises a cartridge for containing said coilable structure; and wherein the means for guiding the tape comprises a pair of justaposed, vertical channels in which the rows of beads at the edges of the tape can ride, the channels being integral with the cartridge; and wherein the means for holding the end portion of the coilable structure comprises a pair of leaf springs, each formed as a part of one of said channels, and biased toward the opposite wall of its channel, so that said beads are confined between the springs and the channel walls.

30. The apparatus of claim 29 further including means for returning the cams to their original positions after being moved by the movable top plate.

31. The apparatus of claim 26 wherein the means for advancing the next end segment of floss to replace one that has been removed comprises: a pair of cams, operatively attached to the housing for sliding motion and positioned to be operated by the movable top plate, substantially perpendicularly thereto; spring means attached to each cam and biased toward the juncture between adjacent beads near the end of the coilable structure, whereby the coilable structure is automatically advanced when the top plate is moved aftwardly by an applicator.

32. The apparatus of claim 1 wherein part of the housing means comprises a cartridge for storing a coilable structure, said cartridge being removable from the rest of the housing means and defining an opening through which the coilable structure is accessible to said means for manipulating it.

33. The apparatus of claim 32 wherein the housing is open at the bottom and the cartridge is inserted through the opening; and further including a transverse support member, fastened into the cartridge, having a raised central portion for supporting the central portion of a coilable structure of the type wherein parallel, transverse segments of dental floss are mounted to a flexible tape, the central portion of the transverse support member extending upwardly through the opening in the cartridge, so that it is interposed between the means for compressing and guiding the prongs of an applicator and the means for controlling the expansion thereof on the housing, so that a segment of dental floss supported on said central portion can be grasped by the compressed prongs of an applicator prior to their entering the means for controlling their expansion.

34. A dental floss cartridge for insertion into an apparatus for loading dental floss from the cartridge onto an applicator, comprising:

a container;

a coilable structure stored in the container and containing segments of dental floss, wherein each segment of floss is perpendicular to the longitudinal axis of the coilable structure and has a bead fixed to each of is ends, and means for providing access to the coilable structure, so that it can be manipulated by said apparatus.

35. Apparatus for using dental floss comprising:

a coilable structure containing dental-floss segments arranged perpendicular to the longitudinal axis of the coilable structure, each segment having a bead fixed to each of its ends;

an applicator of the type having a handle, a pair of resilient prongs fastened to the handle, and means on the end portions of the prongs for grasping a segment of floss and retaining the beads thereof;

housing means for storing the coilable structure;

means for manipulating the coilable structure, so that a floss segment can be positioned, relative to the housing, for being grasped by the means for guiding and compressing the prongs of the applicator so that it can grasp a floss segment; and means for controlling expansion of the prongs after the floss segment has been grasped, so that the beads thereon are retained by the prongs.

* * * * *